United States Patent [19]

Welbourn et al.

[11] Patent Number: 4,645,922
[45] Date of Patent: Feb. 24, 1987

[54] INTEGRATING SPHERE ARRANGEMENT FOR PRODUCING SIZE-CORRECTED COLOR SIGNALS

[75] Inventors: Christopher M. Welbourn; Martin P. Smith, both of Maidenhead; Andrew D. G. Stewart, Reading, all of England

[73] Assignee: Spandrel Establishment, Vaduz, Liechtenstein

[21] Appl. No.: 784,623

[22] Filed: Oct. 4, 1985

[30] Foreign Application Priority Data

Oct. 5, 1984 [GB] United Kingdom ............... 8425274

[51] Int. Cl.⁴ ........................... G01J 3/50; G01J 1/04
[52] U.S. Cl. ................................ 250/226; 250/228; 356/73; 356/236; 356/407; 356/416
[58] Field of Search ............... 356/236, 335, 336, 73, 356/218, 402, 407, 416, 419, 425, 406; 250/226, 228; 209/580, 581, 582

[56] References Cited

U.S. PATENT DOCUMENTS

| 3,432,243 | 3/1969 | Hardesty | 250/228 |
| 3,712,469 | 1/1973 | Dwyer et al. | 209/580 |
| 3,936,189 | 2/1976 | De Remigis | 356/73 |
| 4,131,540 | 12/1978 | Husome et al. | 356/407 |
| 4,235,342 | 11/1980 | Braham | 250/226 |

FOREIGN PATENT DOCUMENTS

| 0041348 | 12/1981 | European Pat. Off. |
| 62178 | 2/1961 | South Africa. |
| 631880 | 5/1962 | South Africa. |
| 643396 | 9/1950 | United Kingdom. |
| 885283 | 12/1961 | United Kingdom. |
| 1131852 | 10/1968 | United Kingdom. |
| 1192765 | 5/1970 | United Kingdom. |
| 2010474 | 6/1979 | United Kingdom. |
| 2018419 | 10/1979 | United Kingdom. |
| 1560446 | 2/1980 | United Kingdom. |
| 2151018 | 7/1985 | United Kingdom. |

*Primary Examiner*—David C. Nelms
*Assistant Examiner*—William L. Oen
*Attorney, Agent, or Firm*—Kerkam, Stowell, Kondracki & Clarke

[57] ABSTRACT

In order to color sort objects such as peas or sweets, they are dropped in succession through two integrating spheres. In the first sphere, the object absorbs infra-red radiation and the peak reduction in infra-red flux is detected in order to provide a signal responsive to the size of the object. In the second sphere, the object is illuminated with white light and the peak reduction in flux is detected by at least three detectors for three colors determined by filters. To make the illumination more uniform in the sphere, there is a step around the sphere almost half way down, with light sources equispaced around the step. The size signal is divided into the respective color signal in a micro-processor to produce a size-corrected color signal.

24 Claims, 7 Drawing Figures

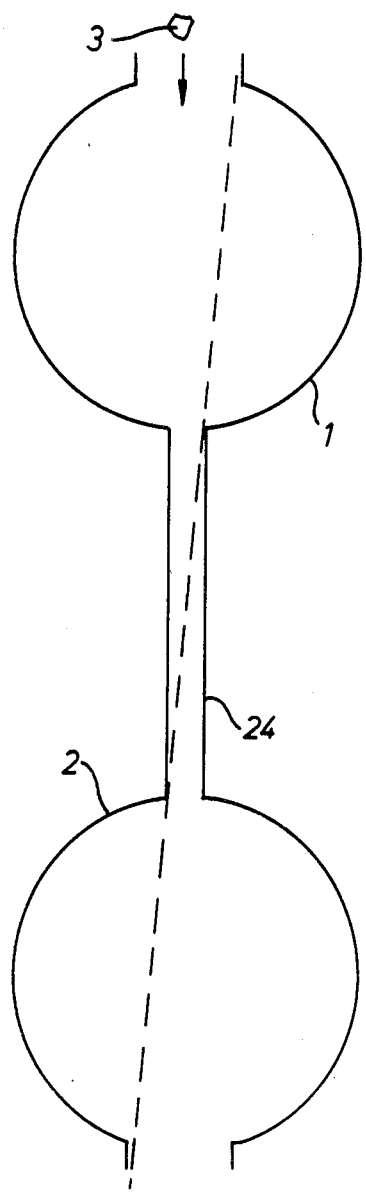
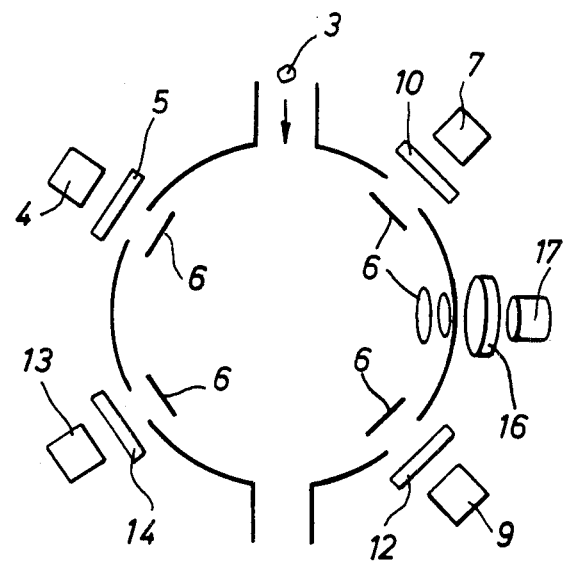
FIG. 2.
FIG. 3.

ize-corrected color signals.

INTEGRATING SPHERE ARRANGEMENT FOR PRODUCING SIZE-CORRECTED COLOR SIGNALS

BACKGROUND OF THE INVENTION

The present invention relates to an apparatus and a method for producing signals responsive to the colour of each of a succession of objects being examined. The objects may for instance be edible products such as peas or sweets, but the invention is in no way limited to edible products. Colour can be any or all of: hue, saturation and lightness.

The measurement of colour of irregular or complex-shaped transparent or reflecting objects presents problems. The light scattered by such objects may be collected by an integrating sphere whilst the object is illuminated from a specific direction, but this has the disadvantage that the direction of illumination is arbitrary and different orientations of the object may lead to different results being obtained. Alternatively, the object may be illuminated diffusely whilst being viewed from one or a number of specific directions, again leading to the same disadvantage.

THE INVENTION

The invention provides apparatus for producing signals responsive to the colour of each of a succession of objects being examined, comprising an integrating cavity; means for feeding the objects one by one through the integrating cavity; means for illuminating with light the interior of the integrating cavity such that the light strikes a surface in the integrating cavity before striking the object being examined; means associated with the integrating cavity for producing an uncorrected or absorption signal responsive to the reduction in visible light flux of at least one particular colour or band of colours due to the presence of the object in the integrating cavity; means for producing a size signal responsive to the size of the object being examined; and means responsive to the uncorrected colour signal or absorption signal and to the size signal for producing a corrected colour signal.

The invention also provides a method of producing signals responsive to the colour of each of a succession of objects being examined, comprising: feeding the objects one by one through an integrating cavity whose interior is illuminated with light which strikes a surface in the integrating cavity before striking the object being examined; producing an uncorrected or absorption signal responsive to the reduction in visible light flux of at least one particular colour or band of colours due to the presence of the object in the cavity; producing a size signal responsive to the size of the object being examined; and correcting the uncorrected colour signals or absorption signals by means of the size signals to produce corrected signals responsive to the colour of each successive object.

The use of the integrating cavity diffusely illuminates the object and enables the light scattered by the object to be collected over a large solid angle. As small objects of intense colouration would produce effects comparable to those produced by larger objects of lesser colouration, a signal is produced responsive to the size of the object. The appropriate size parameter depends upon the nature of the optical properties of the object; the parameter could be, or be substantially proportional to, for instance the volume, or the projected area of the surface area, or a value which is a function both of the volume and/or the surface area. The volume could be simply determined by weighing. However, the surface area gives a good measurement and enables one to provide a very compact apparatus.

The invention further provides an integrating cavity for sensing a parameter of an object in a central zone thereof, the integrating cavity having an annular step around the central zone and means being provided for illuminating with electromagnetic radiation the interior of the integrating cavity, the illuminating means being distributed around the step and projecting radiation generally axially of the annulus defined by the step such that the radiation strikes a surface in the integrating cavity before entering the central zone.

The special illuminating cavity provides more uniform illumination, especially for the situation in which the total area of apertures in the cavity is large, say over 2%, in relation to the surface area of the walls of the cavity.

PREFERRED EMBODIMENTS

The invention will be further described, by way of example, with reference to the accompanying drawings, in which:

FIGS. 1, 2 and 3 are schematic vertical sections through three different apparatuses in accordance with the invention.

FIG. 1

Figure 1:
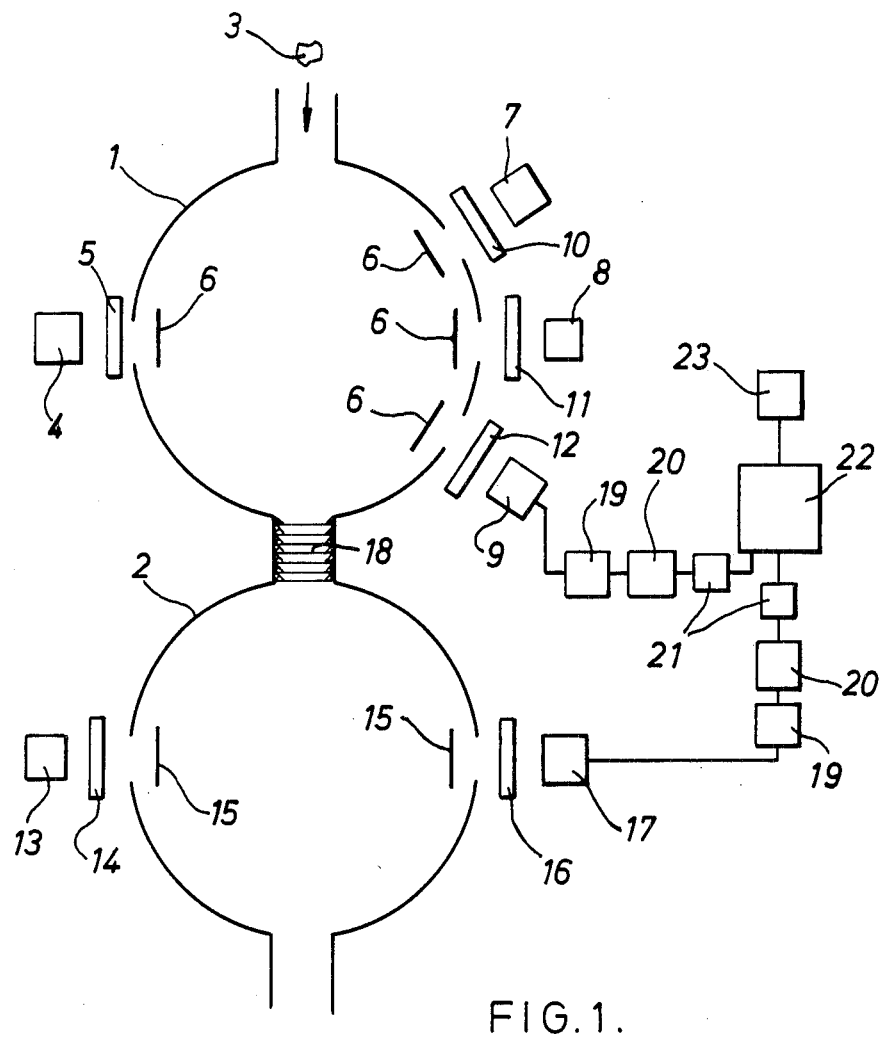

The apparatus of FIG. 1 has two integrating cavities or spheres 1,2 mounted directly one above the other with a central passageway for the passage of objects 3 being examined. The first integrating sphere 1 has an illuminating lamp 4 associated with a filter 5 and a baffle 6 such that the whole interior wall of the sphere 1 is bathed in white light which is uniform in intensity and direction. The light strikes the baffle 6 before striking the object 3, though in an alternative arrangement, it can be directed onto the internal wall of the sphere 1; in each case, the light strikes a surface in the sphere 1 before entering the central zone of the sphere 1. The lamp 4 can be associated with a fibre optic illuminator and a useful colour temperature is 2857° K. (CIE source A), the filter 5 being a conversion filter to give a spectral distribution substantially equivalent to daylight.

When the object 3 is introduced into the sphere 1, it subtracts the appropriate amount of light at the appropriate wavelengths, according to its colour, and the reduction in flux in the sphere 1 is used to determine the colour.

Normally, there will be means for producing colour signals (uncorrected colour signals or absorption signals) responsive to the reduction in flux of at least three colours or bands of colours. The particular wavelengths or wavelength bands chosen may depend upon the objects being examined. For instance, if the objects are edible such as peas or sweets, simple blue, green and red reponse can be determined. In this case, there are three photo-detectors 7,8,9 associated respectively with a filter 10 which may be Chance-Pilkington OB 10 (blue), a filter 11 which may be Schott NG 5 (neutral) and Schott VG 9 (green), and Schott RG 590, and a filter 12 which may be Schott BG 28 (both combined, to give red) and NG 4 (neutral). If extra discrimination is required (as for instance could be the case when examining crystalline material such as gem stones, particularly diamonds), a signal responsive to the reduction in flux of a further colour or colours may be introduced—for instance violet (filters OB 10 and Chance-Pilkington OV 1)—for extra discrimination in specific spectral regions. In general, the filters 10,11,12, and the filter 5 are chosen to approximate to the desired CIE colour matching functions. The photo detectors 7,8,9 may be silicon detectors.

The second sphere 2 is used to estimate the size of the object 3, and has a radiation source 13, a filter 14, baffles 15, a further filter 16 and a detector 17. The wavelength passing the filter 14 is chosen such that the object 3 is substantially opaque or intrinsically absorbing at that wavelength, the peak reduction in flux being a measure of the size of the object; if the absorption coefficient is large, the size signal will be substantially related to the surface area of the object; if the absorption coefficient is small, the size signal will be substantially related to the volume of the object. Frequently, ultra-violet radiation of infra-red radiation is absorbed by the object. For instance, one could use ultra-violet below 220 nm with an ultra-violet detector 17; one could use a heated black body with an infra-red detector 17 sensitive to around 5000 nm.

As some objects 3 may give luminescence under ultra-violet light, and more generally, it may be beneficial to provide means for preventing transmission of radiation from the sphere 2 to the sphere 1. A simple radiation trap 18 is indicated in FIG. 1. Placing the ultra-violet measuring sphere 2 downstream of the visible-light measuring sphere prevents persistant phosphorescence from interfering with the visible-light measurement (the reverse is preferred when using infra-red, see FIG. 4).

The outputs of the detector 7,8,9 and 17 are each passed via a negative gain amplifier 19, a peak response component 20 and an analogue/digital converter 21 to a micro-processor 22. In the micro-processor 22 the uncorrected colour signal in each channel associated with the sphere 1 is divided by the size signal from the sphere 2. The different responses of each of the colour channels (resulting from lamp intensity variation with wave length, detector response variation with wave length and differing areas under the transmission spectrum of each set of filters) are normalised by inserting black objects; thereby coefficients are derived for weighting the signals from each of the colour channels. The colour signal, corrected by size, can be used in any appropriate manner; however, it is preferred to use standard CIE colorimetry techniques to obtain tristimulus values and chromacity coordinates, and thereby to combine the outputs from each channel. The output of the micro-processor 22 (corrected colour signal) can be used to give an actual indication of colour, but is preferably used to drive a sorter 23 which for instance rejects badly coloured foodstuffs or sorts the objects 3 into different colour gradings—a simple form of sorter is using a ring of nozzles around the path of the objects 3, the appropriate nozzle being actuated to blow the object 3 into the required bin. Sorting into a large number (e.g. twenty) of categories may require more complex dispensing means such as a carousel dispensing device.

An alternative to selecting peak values of flux reduction is to select the integrated reduction in flux with respect to time (integral of the flux reduction with respect to time).

As the change in signal is proportional to the ratio of the total surface area of the object 3 to the internal area of the sphere 1 (or 2), the dimensions of the sphere 1 (or 2) should be as small as practicable. A ratio of $1:10^3$ surface area object 3: internal area sphere 1 (and 2) can be aimed at, though $1:10^4$ is not excessive. With an object 3 of diameter about 2 mm, a sphere 1 (and 2) of 50 mm internal diameter can be used.

The sphere 1 can be coated in barium sulphate photometric paint of neutral spectral reflectance; the coating of the sphere 2 depends upon the radiation used—for ultra-violet it can be as for the sphere 1, for infra-red, it can be matt gold.

FIG. 2

FIG. 2 is included to illustrate that the radiation trap between the sphere 1,2 can be arranged in another way. In this case there is an extended tube 24 with a black surface, it will act as a radiation trap as indicated by the dashed line.

FIG. 3

FIG. 3 illustrates that a single sphere 1 can be used, even with ultra-violet which is provoking photoluminescence, providing some arrangement is made for preventing the photoluminescence interfering with the colour measurements, or in more general terms for ensuring that the colour signal-producing means is not responsive to the radiation used for size response—likewise the size signal-producing means should not be responsive to the light used for colour response. In this case, the lamps 4,13 are pulsed and the arrangement is such that the circuits associated with the detector 7,8,9 are not responsive when the lamp 13 is pulsed (nor in a short decay period afterwards), and the circuit associated with the detector 16 is not responsive when the lamp 4 is pulsed. However, as a further refinement, the circuit associated with one or more of the detectors 7,8,9 may be responsive when the lamp 13 (if ultra-violet) is pulsed so as to produce a separate signal responsive to the luminescence excited by the ultra-violet radiation.

FIGS. 4 TO 6

Figure 4:
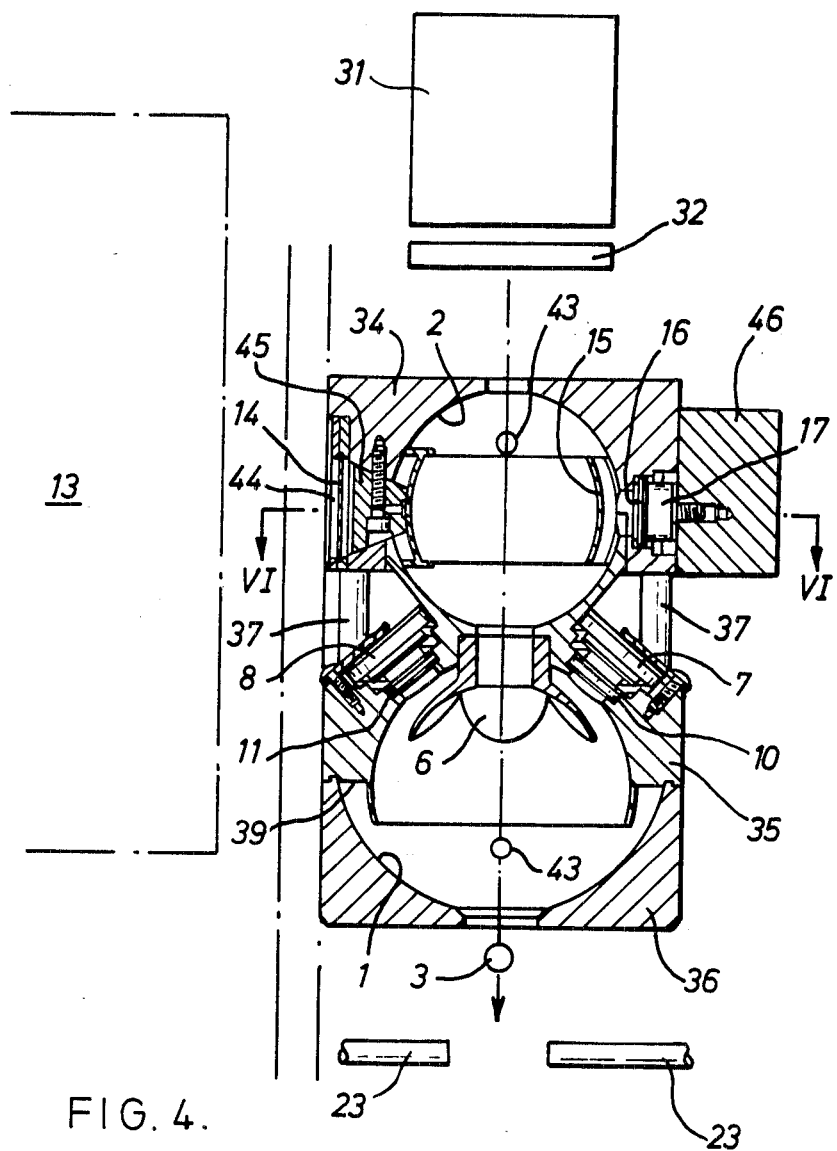
FIG. 4 is a vertical section through a fourth apparatus in accordance with the invention, along the line IV—IV in FIGS. 5 and 6.
Figure 5:
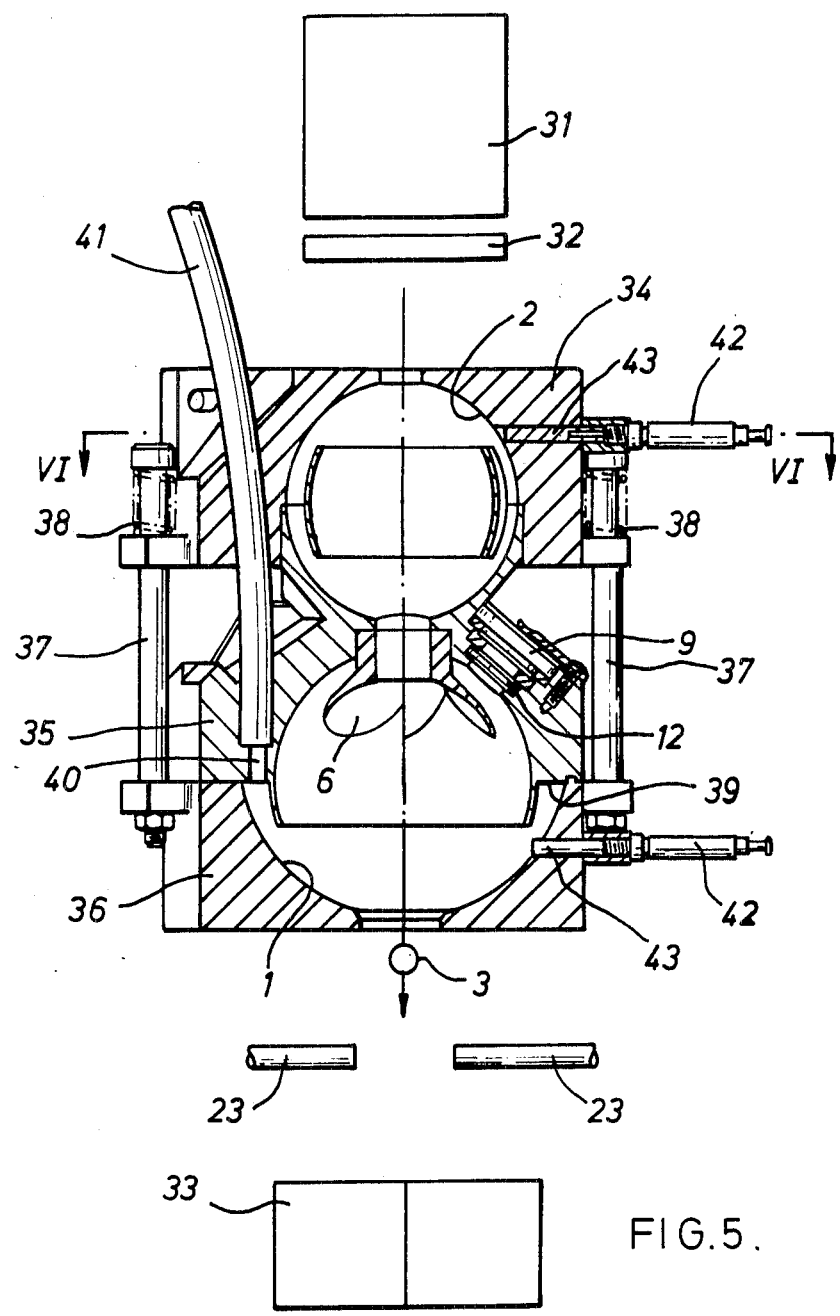
FIG. 5 is a vertical section through the fourth apparatus, along the line V—V in FIG. 6.
Figure 6:
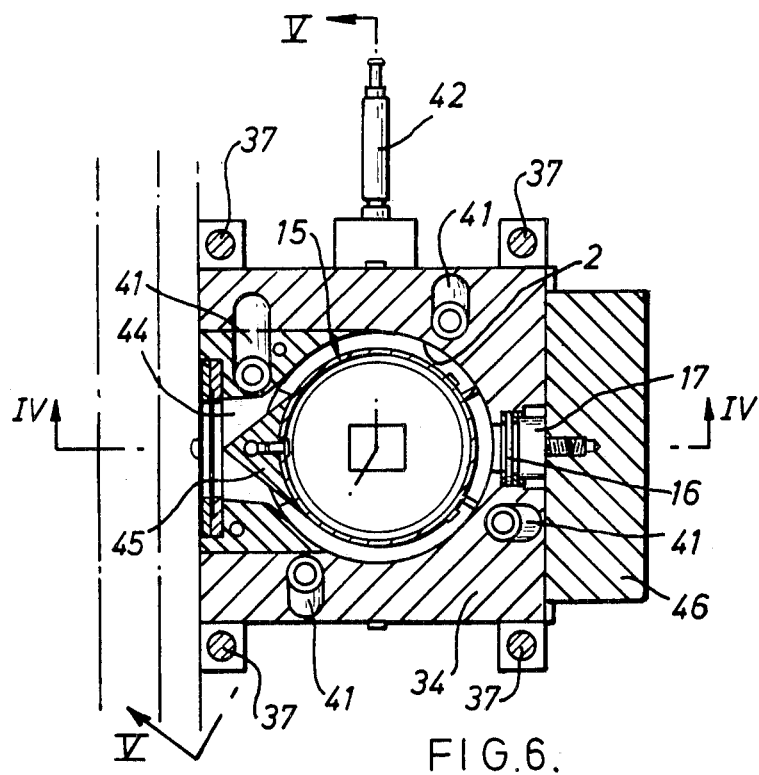
FIG. 6 is a horizontal section through the fourth apparatus, along the line VI—VI in FIGS. 4 and 5.

The apparatus of FIGS. 4 to 6 is a working prototype. Where appropriate, the same references have been used as for FIGS. 1 to 3, and in general principle the apparatus is very similar to that of FIG. 1 except that the integrating spheres 1,2 are reversed.

The objects are released or projected downwards in rapid succession by a feeder 31, along a vertical path defined through the apparatus. The feed 31 is only shown schematically as suitable feeders are available. The speed of the objects as they leave the feeder may be about 1 m/s, and the rate of feed around ten objects per second. Immediately below the feeder 31, there is a light curtain 32 for signalling to the micro-processor 22 (FIG. 1) that an object is approaching the first integrating sphere 2.

Below the integrating sphere 1, there is a suitable sorting means 23 and a number (e.g. twenty) bins 33.

The sorting means 23 will be controlled by the output of the micro-processor 22.

The integrating spheres 1,2 each have a hollow casing formed in three parts 34,35,36, as best seen in FIG. 5. The parts are held together by rods 37 which are spring-loaded by helical compression springs 38. The parts 35,36 define an annular step 39 in the internal surface of the integrating sphere 1, which is provided with a short skirt. Illuminating means are evenly distributed around the step 39, in this case in the form of four fibre-optic light sources 40 having fibre conductors 41; as an alternative, a unitary fibre-optic ring may be used, providing uniform illumination all the way round the step 39. The arrangement of the step 39 provides uniform illumination in the sphere 1, in spite of the fact that the total aperture area is about 3% of the total area of the internal wall of the sphere 1.

The sphere 1 is provided with four equi-spaced photo-detectors 7,8,9 (the fourth not being visible) with respective filters 10,11,12 (the fourth again not being visible). These are shielded by lobar baffles 6 formed in one piece which is retained in the middle part 35. The integrating sphere 1 is provided with a calibration cylinder 42; actuating the cylinder 42 causes movement of a small normalising piston 43 which projects somewhat into the integrating sphere 1, for calibration of the integrating sphere 1. The piston 43 will be painted black or can be black-anodised stainless steel or aluminium.

The integrating sphere 2 has a similar normalising cylinder 42 and piston 43. The baffle 15 in the integrating sphere 2 is in the form of an annular baffle spaced inwardly from the internal wall of the sphere 2, infrared radiation being projected behind the annular baffle 15. In this case, the radiation is taken from an infra-red black body radiator 13 placed adjacent an opening 44 in the side of the integrating sphere 2. Mounted in the opening 44 is a wedge-shaped mirror 45 with the apex facing outwards, dividing the radiation and reflecting it, mainly onto the internal wall of the integrating sphere 2 but partly onto the baffle 15. There is a filter 14 to filter out any visible or ultra-violet radiation. The integrating sphere 2 has an infra-red detector 17 which may be sensitive to around 5000 nm, and has a filter 16 to filter out any visible radiation (from outside or from the integrating sphere 1) or ultra-violet radiation. An advantage of placing the infra-red sphere 2 before the visible radiation sphere 1 is that any slight heating of the objects in the visible radiation sphere 1 does not distort the estimate of size in the sphere 2. The integrating sphere 2 is associated with a heat sink 46 to dissipate the heat from the detector 17.

Although the step 39 has been described above in relation to the visible radiation sphere, it could be applied to a sphere in which say a size is estimated using infra-red or ultra-violet radiation. Likewise, although the annular baffle 15 and wedge-shaped mirror 45 have been applied to the infra-red sphere, they could be applied to the visible radiation sphere.

FIG. 7

Figure 7:
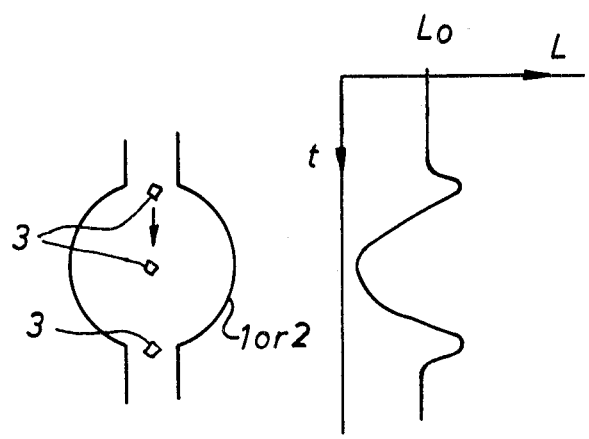
FIG. 7 illustrates graphically the change in flux as an object drops through each sphere of the apparatus.

FIG. 7 merely illustrates the light level as an object 3 drops through the sphere 1 or 2. The light level L is plotted against time t; $L_o$ is the steady state. The large trough due to absorption is clearly visible. It will also be seen that as the object 3 enters the sphere 1 or 2 and leaves the sphere 1 or 2, there is an increase in flux due to reflection. From the increase in flux, information can be derived about the surface structure and reflectivity of the object 3. In particular, if the increase in flux at different wavelengths or bands of wavelengths is sensed, information about surface roughness can be obtained—the Rayleigh scattering from surface asperities is inversely proportional to the fourth power of the wavelength; e.g. for visible radiation at 500 nm and for infra-red radiation at 5000 nm, the Rayleigh scattering would differ by a factor of $10^4$. The micro-processor 22 can be arranged to provide the required information.

We claim:

1. Apparatus for producing signals responsive to the colour of each of a succession of objects being examined, comprising:

an integrating cavity;

means for feeding the objects one by one through the integrating cavity;

means for illuminating with light the interior of the integrating cavity whereby the light strikes a surface in the integrating cavity before striking the object being examined;

means associated with the integrating cavity for producing an absorption signal responsive to the reduction in visible light flux of at least one particular colour or band of colours due to the presence of the object in the integrating cavity;

means for producing a size signal responsive to the size of the object being examined; and means responsive to said absorption signal and said size signal for correcting said absorption signal in accordance with the size of the respective objects and thereby producing a corrected colour signal responsive to the colour of the said objects being examined.

2. The apparatus of claim 1, and comprising means defining a path through the apparatus along which the objects move while their colour is examined.

3. The apparatus of claim 2 and comprising means for releasing or projecting the objects along said path whereby the objects fall freely or are projected during examination.

4. The apparatus of claim 2, wherein the absorption signal producing means are associated with means for selecting the peak value of said reduction in flux.

5. The apparatus of claim 2, wherein the absorption signal producing means are associated with means for selecting the integral of said reduction in flux with respect to time.

6. The apparatus of claim 1, and further comprising means associated with the integrating cavity for producing a signal responsive to increase in flux as the object enters the integrating cavity and/or leaves the integrating cavity, and means for deriving from the increase in flux, information about the surface structure and reflectivity of the object.

7. The apparatus of claim 6, wherein the flux increase signal-producing means produce signals responsive to the increase in flux at different wavelengths or bands of wavelengths.

8. Apparatus for producing signals responsive to the colour of each of a succession of objects being examined, comprising:

an integrating cavity;

means for feeding the objects one by one through the integrating cavity;

means for illuminating with light the interior of the integrating cavity whereby the light strikes a surface in the integrating cavity before striking the object being examined;

means associated with the integrating cavity for producing an absorption signal responsive to the reduction in visible light flux of at least one particular colour or band of colours due to the presence of the object in the integrating cavity;

means for producing a size signal responsive to the size of the object being examined; and means repsonsive to said absorption signal and said size signal for correcting said absorption signal in accordance with the size of the respective objects and thereby producing a corrected colour signal responsive to the colour of the said objects being examined; wherein the size signal-producing means comprise an integrating cavity, means for projecting radiation into the integrating cavity, and means for responding to a wavelength or band of wavelengths which the objects absorb to a substantial degree.

9. The apparatus of claim 8, wherein the size response radiation is ultra-violet radiation.

10. The apparatus of claim 8, wherein the size response radiation is infra-red radiation.

11. The apparatus of claim 8, and comprising two said integrating cavities, namely the first-mentioned integrating cavity in which colour is examined and the second-mentioned integrating cavity in which size is examined.

12. The apparatus of claim 11, wherein the first-mentioned integrating cavity is downstream of the second-mentioned integrating cavity.

13. The apparatus of claim 8, wherein the absorption signal producing means is unresponsive to the radiation used for size response and the size signal producing means is unresponsive to the radiation used for absorption response.

14. The apparatus of claim 13, wherein the size response radiation and the absorption response light are pulsed, the absorption signal producing means and the size signal producing means being responsive when the respective light or radiation is present.

15. The apparatus of claim 14, wherein the size response radiation is ultra-violet radiation, and comprising means associated with the uncorrected colour signal producing means for producing a signal responsive to luminescence excited by the ultra-violet radiation.

16. The apparatus of claim 1, and including means responsive to the signals produced by the corrected colour signal producing means for determining a path followed by successive objects after examination, thereby enabling the objects to be automatically sorted in accordance with their colour.

17. The apparatus of claim 1, wherein the integrating cavity includes an annular step around the path of the objects and the illuminating means projects electromagetic radiation from the step, the illuminating means being distributed around the step.

18. The apparatus of claim 17, wherein there is a plurality of the illuminating means distributed around the annular step.

19. The apparatus of any of claim 8, wherein the size responsive integrating cavity defines an opening in its side for receiving electromagnetic radiation, there being mounted in the opening a wedge-shaped mirror with the apex facing outwards, to divide the radiation and reflect it.

20. The apparatus of claim 1 or 8, wherein a said integrating cavity has an annular baffle mounted therein, spaced inwardly from the internal wall of the integrating cavity, the illuminating or projecting means projecting electromagnetic radiation behind the annular baffle.

21. The apparatus of claim 1, wherein said size signal responsive means are responsive to the total surface area of the respective objects.

22. The apparatus of claim 1, wherein said means for correcting said absorption signal comprise means for dividing said absorption signal by said size signal.

23. An integrating cavity for sensing a parameter of an object in a central zone thereof, the integrating cavity having a hollow casing defining an internal surface which in turn defines an annular step around said central zone, means being provided for illuminating with electromagnetic radiation the interior of the integrating cavity, the illuminating means being distributed around the step and projecting radiation generally axially of the annulus defined by the step such that the radiation strikes a surface in the integrating cavity before entering the central zone.

24. A method of producing signals responsive to the colour of each of a succession of objects being examined, comprising:

feeding the objects one by one through an integrating cavity whose interior is illuminated with light which strikes a surface in the integrating cavity before striking the object being examined;

producing an adsorption signal responsive to the reduction in visible light flux of at least one particular colour or band of colours due to the presence of the object in the cavity;

producing a size signal responsive to the size of the object being examined; and correcting the absorption signals by means of the size signals to produce corrected signals responsive to the colour of each successive object.

* * * * *